(12) United States Patent
Polonka et al.

(10) Patent No.: US 7,780,954 B2
(45) Date of Patent: Aug. 24, 2010

(54) GLOW AND SUNLESS TANNING COLOR ENHANCEMENT BY CATIONIC COPOLYMERS

(75) Inventors: Jack Polonka, Peekskill, NY (US); John Brian Bartolone, Bridgeport, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 178 days.

(21) Appl. No.: 12/128,642

(22) Filed: May 29, 2008

(65) Prior Publication Data

US 2009/0208430 A1     Aug. 20, 2009

Related U.S. Application Data

(60) Provisional application No. 61/029,649, filed on Feb. 19, 2008.

(51) Int. Cl.
*A61Q 17/04*     (2006.01)
*A61K 8/02*      (2006.01)
*A61K 31/785*    (2006.01)
*A61K 31/121*    (2006.01)
*A61K 31/14*     (2006.01)
*A01N 35/02*     (2006.01)
*A01N 33/12*     (2006.01)

(52) U.S. Cl. ............... 424/59; 424/401; 424/78.03; 424/78.08; 514/675; 514/642

(58) Field of Classification Search ............... None
See application file for complete search history.

(56) References Cited

U.S. PATENT DOCUMENTS

| 4,676,913 | A |   | 6/1987  | Easterly, Jr. et al. |
|-----------|---|---|---------|---------------------|
| 5,051,487 | A |   | 9/1991  | Bhattacharyya et al. |
| 5,232,688 | A |   | 8/1993  | Ziegler et al. |
| 5,637,306 | A |   | 6/1997  | Cauwet et al. |
| 5,700,452 | A | * | 12/1997 | Deckner et al. ............... 424/59 |
| 6,277,892 | B1 |  | 8/2001  | Deckner et al. |
| 6,344,185 | B1 | * | 2/2002 | Argus et al. ............... 424/59 |
| 6,432,389 | B1 |  | 8/2002  | Hansenne et al. |
| 6,664,287 | B2 | * | 12/2003 | Avery et al. ............... 514/436 |
| 7,015,279 | B2 | * | 3/2006 | Braun et al. ............... 524/815 |
| 2005/0014893 | A1 | * | 1/2005 | Braun et al. ............... 524/801 |
| 2008/0025939 | A1 |  | 1/2008 | Cassier et al. |
| 2008/0051492 | A1 |  | 2/2008 | Mitarotonda et al. |
| 2008/0078036 | A1 |  | 4/2008 | Rondeau |
| 2008/0131385 | A1 |  | 6/2008 | Roso et al. |
| 2009/0074823 | A1 | * | 3/2009 | Takakura ............... 424/401 |

FOREIGN PATENT DOCUMENTS

| WO | 94/02176      | 2/1994 |
| WO | 00/53815      | 9/2000 |
| WO | 2005/027862 A1 | 3/2005 |

OTHER PUBLICATIONS

Co-pending application—Polonka et al. U.S. Appl. No. 61/029,654, filed Feb. 19, 2008.
Co-pending application—Polonka et al. U.S. Appl. No. 61/029,657, filed Feb. 19, 2008.
International Search Report PCT/EP2009/051024.
Holden, C., "Formulating Hair and Skin Products more Effectively", Speciality Chemicals, Redhill, GB, vol. 16, No. 1, Jan. 1, 1996, pp. 21-23; XP002071540.
Aseyev V.O. et al., "Collapse of poly(methacryloylethyl trimethylammonium methylsulfate) on addition of acetone into an aqueous solution" Polymer, Elsevier Science Publishers B.V. GB, vol. 40, No. 5, Mar. 1, 1999, pp. 1173-1180; XP004141096.

* cited by examiner

*Primary Examiner*—Ernst V Arnold
*Assistant Examiner*—Jessica Kassa
(74) *Attorney, Agent, or Firm*—Milton L. Honig

(57) ABSTRACT

A cosmetic composition for sunless tanning or imparting glow to skin is herein described. The composition includes from about 0.1 to about 20% by weight of a tanning agent and from 0.1 to 20% by weight of a crosslinked cationic copolymer having a monomer unit which is a methacryloylethyl or acryloylethyl tri($C_1$-$C_3$ alkyl)ammonium salt. The crosslinked cationic copolymer is a color enhancing agent which improves color intensity and avoids streaking of the developing tan/glow.

7 Claims, No Drawings

GLOW AND SUNLESS TANNING COLOR ENHANCEMENT BY CATIONIC COPOLYMERS

BACKGROUND OF THE INVENTION

1. Field of the Invention

The invention concerns a product for imparting glow and/or a sunless tan to skin. The product includes besides a skin tanning agent also a color enhancement agent for reducing the time to full maturation and deeper color intensity.

2. The Related Art

Today there is a great health concern with natural tanning through sunlight. Ultraviolet radiation from the sun is considered to be a leading factor in causing skin cancer. Even if not lethal, ultraviolet radiation has been acknowledged as accelerating aging and wrinkling processes on the skin.

Beyond health concerns, there are obvious practical reasons against natural tanning. Foremost is the reason that in many areas of the globe and during all but summertime, there is insufficient sunlight available to accomplish the task.

While some choose artificial sunlight as an alternative to exposure to natural sunlight, and as a potentially less risky means of obtaining a tan, this option too is not always suitable; hence, other options for skin tanning are desirable. One of these options, to which people are turning in increasing numbers, are the various "sunless tanning compositions" that can be used to brown human skin without the necessity of exposing the skin to natural, or artificial, sunlight. Such compositions contain, as their active agent, one or more of the available self tanning agents, including dihydroxyacetone ("DHA," 1,3-dihydroxy-2-propanone).

DHA, currently the most widely used of the self tanning agents, is believed to exert its effect through interactions between its hydroxyl groups and the amino groups of amino acids and peptides naturally occurring in the hydrolipid pellicle and first layers of the stratum corneum of the skin. Such Maillard reactions are believed (see, e.g., Bobin et al., J. Soc. Cosmet. Chem. 35: 255 (1984)) to lead to formation of brown pigments in the skin, thereby giving it an appearance similar to that of a naturally obtained tan.

Although there has been great progress in sunless self-tanning as noted above, considerable further progress is needed to increase speed of coloration and achieve a coloration even closer to a natural look. Furthermore, many of the known self-tanning compositions have poor substantivity. Rub-off onto clothing may occur and thereby impart a stain to the textiles. Many of the formulas are subject to wash-off and sweat-off after their application. There is a need to improve substantivity on the skin. Streaking is also a problem faced by the art. By the term "streaking" is meant noneven deposition on the skin; the coloration tends to migrate along an outer perimeter as a result of the formula being rubbed around upon the skin.

New approaches are required to address one or more of the problems with self-tanning compositions. Thus, the present invention is directed to both a product and method which solves the problem of slow rates of coloration. In certain embodiments the invention imparts a more intense (darker) color not achievable with traditional sunless tanning agents.

SUMMARY OF THE INVENTION

A cosmetic product for imparting a glow or sunless tan to skin is provided which includes:

(i) from about 0.1 to about 20% by weight of a tanning agent which is reactive with skin to produce a tan color;

(ii) from about 0.1 to about 20% by weight of a color enhancing agent which is a crosslinked cationic copolymer having monomer units of methacryloylethyl or acryloylethyl tri($C_1$-$C_3$ alkyl) ammonium salt; and (iii) a cosmetically acceptable carrier.

DETAILED DESCRIPTION OF THE INVENTION

Now it has been found that crosslinked cationic copolymers partially formed from monomer units of methacryloylethyl or acryloylethyl tri($C_1$-$C_3$ alkyl)ammonium salts are effective color enhancing agents in imparting glow (radiance) and/or sunless tan to skin. The combination of a tanning agent and the cationic copolymer deliver a more intense color to the treated area of skin. Further, substantivity is enhanced. There is resistance to the tanning agent being washed-off or sweated off. Physically it is also more difficult to rub-off the compositions onto clothing.

Tanning agents of the present invention are materials which when applied to human skin will react with amino acids of the skin so as to form pigmented species (i.e. a tan). These reactions give skin a brown appearance similar to a color obtained by exposure to sunlight. These materials may be alpha-hydroxyaldehydes and ketones, glyceraldehyde, troxerutin and related alcohol aldehydes, various indoles, imidazoles and derivatives thereof. Illustrative but not limiting are dihydroxyacetone, melanin, mahakanni (eclipta alba), methyl glyoxal, erythrulose, alloxan, 2,3-dihydroxysuccindialdehyde and mixtures thereof. More preferred is dihydroxyacetone.

Amounts of the tanning agent may range from about 0.1 to about 20%, preferably from about 0.5 to about 10%, more preferably from about 0.8 to about 5%, and optimally from 1 to 2% by weight of the cosmetic composition.

Formulations intended for imparting glow (synonymous with radiance), utilize tanning agent at lower levels such as from 0.5 to 2.5% by weight. Sunless tanning to a relatively dark shade ordinarily requires the tanning agent to be at the higher levels from 3 to 20% by weight.

Cationic copolymers of the present invention incorporate as one of the repeating units a methacryloylethyl tri($C_1$-$C_3$ alkyl) ammonium salt or an acryloylethyl tri($C_1$-$C_3$ alkyl) ammonium salt. The term "salt" for this monomer unit may be but is not limited to chloride, bromide, sulfate, sulphonate, methosulfate, nitrate, tosylate, phosphate and phosphonate. The term "copolymer" means at least two different monomer repeating units, preferably three or more different monomer repeating units. Monomer units that crosslink are particularly useful.

Monomers forming the copolymer with the methacryloylethyl or acryloylethyl tri($C_1$-$C_3$ alkyl) ammonium salt monomer units include: styrene, acrylic acid, methacrylic acid, vinyl chloride, vinyl acetate, vinyl pyrrolidone, isoprene, vinyl alcohol, vinyl methylether, chloro-styrene, dialkylamino-styrene, maleic acid, acrylamide, methacrylamide, tris(hydroxymethyl)-acrylamidomethane and mixtures thereof. Where the term "acid" appears, the term means not only the free acid but also $C_1$-$C_{30}$ alkyl esters, anhydrides and salts thereof. Preferably but not exclusively the salts thereof may be ammonium, alkanolammonium, alkali metal and alkaline earth metal salts. Most preferred are the ammonium and alkanolammonium salts of acid monomers.

Most preferred for purposes of this invention as the crosslinked cationic copolymer is acrylamide/acryloylethyl trimethylammonium chloride/tris(hydroxymethyl)-acrylamidomethane copolymer. Commercial availability is under the trademark 7688 MP available from Seppic Inc.

Number average molecular weight of the copolymers according to the invention may range from about 1,000 to about 3,000,000, preferably from about 3,000 to about 100,000, optimally from about 10,000 to about 80,000.

Amounts of the copolymer may range from about 0.1 to about 20%, preferably from about 0.5 to about 10%, more preferably from about 1 to about 7%, and optimally from about 1.5 to about 5% by weight of the composition.

Additional enhancement of tanning effect and elimination of streaking can be achieved by utilization of a monomeric quaternary ammonium salt. Particularly useful are $C_{12}$-$C_{22}$ fatty alkyl substituted ammonium salts. These may be mono-fatty alkyl or di-fatty alkyl substituted ammonium compounds. Amounts may range from about 0.01 to about 5%, preferably from about 0.05 to about 3%, and optimally from about 0.15 to about 1% by weight of the cosmetic compositions. An illustrative material is distearyl dimethyl ammonium salts, and in particular distearyl dimonium chloride sold under the trademark Varisoft TA-100.

Compositions of this invention will also include a cosmetically acceptable carder. Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, natural or synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to $0.1 \text{ m}^2/\text{s}$ at 25° C. Among the preferred nonvolatile emollients useful in the present compositions are the polydimethyl siloxanes having viscosities from about $1 \times 10^{-5}$ to about $4 \times 10^{-4}$ $\text{m}^2/\text{s}$ at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

a) Alkyl esters of saturated fatty acids having 10 to 24 carbon atoms. Examples thereof include behenyl neopentanoate, isononyl isonanonoate, isopropyl myristate and octyl stearate.

b) Ether-esters such as fatty acid esters of ethoxylated saturated fatty alcohols.

c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

d) Wax esters such as beeswax, spermaceti wax and tribehenin wax.

e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol.

Thickeners can be utilized as part of the cosmetically acceptable carrier of compositions according to the present invention. Typical thickeners include crosslinked acrylates (e.g. Carbopol 982®)), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Humectants may be employed in the present invention. These are generally polyhydric alcohol-type materials. Typical polyhydric alcohols include glycerol, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from 0.5 to 50%, preferably between 1 and 15% by weight of the composition.

Compositions of the present invention may be in any form. These forms may include lotions, creams, roll-on formulations, sticks, mousses, aerosol and non-aerosol sprays and fabric (e.g. nonwoven textile)-applied formulations. Particularly useful are nonwoven cloths of polypropylene or cotton/polyester impregnated with dihydroxyacetone and a cationic copolymer of the present invention.

Surfactants may also be present in compositions of the present invention. Total concentration of the surfactant when present may range from about 0.1 to about 30%, preferably from about 0.1 to about 15%, optimally from about 0.5 to about 2% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Advantageously present may also be water-insoluble organic material in the form of polymeric porous spherical particles. By the term "porous" is meant an open or closed cell structure. Preferably the particles are not hollow beads. Average particle size may range from about 0.1 to about 100, preferably from about 1 to about 50, more preferably greater than 5 and especially from 5 to about 15, optimally from about 6 to about 10 μm. Organic polymers or copolymers are the preferred materials and can be formed from monomers including the acid, salt or ester forms of acrylic acid and methacrylic acid, methylacrylate, ethylacrylate, ethylene, propylene, vinylidene chloride, acrylonitrile, maleic acid, vinyl pyrrolidone, styrene, butadiene and mixtures thereof. The polymers are especially useful in cross-linked form. Cells of the porous articles may be filled by a gas which can be air, nitrogen or a hydrocarbon. Oil Absorbance (castor oil) is a measure of porosity and in the preferred but not limiting embodiment may range from about 90 to about 500, preferably from about 100 to about 200, optimally from about 120 to about 180 ml/100 grams. Density of the particles in the preferred but not limiting embodiment may range from about 0.08 to 0.55, preferably from about 0.15 to 0.48 g/cm³.

Illustrative porous polymers include polymethylmethacrylate and cross-linked polystyrene. Most preferred is polymethyl methacrylate available as Ganzpearl® GMP 820 available from Presperse, Inc., Piscataway, N.J., known also by its INCI name of Methyl Methacrylate Crosspolymer.

Amounts of the water-insoluble polymeric porous particles may range from about 0.01 to about 10%, preferably from about 0.1 to about 5%, optimally from about 0.3 to about 2% by weight of the composition.

Preservatives can desirably be incorporated into the personal care compositions of this invention to protect against the growth of potentially harmful microorganisms. Particularly preferred preservatives are phenoxyethanol, methyl paroben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.01% to 2% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

Still other suitable actives for skin compositions and use in the present invention include creatine, resveratrol, hyaluronic acid (particularly those of molecular weight of around 800), and combinations thereof. Amounts may range from about 0.000001 to about 5%, preferably from about 0.001 to about 1% by weight of the compositions.

Compositions of the present invention may also contain vitamins. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, ascorbyl tetraisopalmitate, Vitamin E (tocopherol), Vitamin E Acetate and DL-panthenol. Total amount of vitamins when present in compositions according to the present invention may range from 0.001 to 10%, preferably from 0.0% to 1%, optimally from 0.1 to 0.5% by weight of the composition.

Desquamation agents are further optional components. Illustrative are the alpha-hydroxycarboxylic acids and beta-hydroxycarboxylic acids and salts of these acids. Among the former are salts of glycolic acid, lactic acid and malic acid. Salicylic acid is representative of the beta-hydroxycarboxylic acids. Amounts of these materials when present may range from about 0.1 to about 15% by weight of the composition.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1-8

A series of typical body lotions according to the present invention are outlined in Table I below.

TABLE I

| Component | Example (Weight %) | | | | | | | |
|---|---|---|---|---|---|---|---|---|
| | 1 | 2 | 3 | 4 | 5 | 6 | 7 | 8 |
| Glycerin | 12.00 | 10.00 | 10.00 | 12.00 | 12.00 | 12.00 | 8.00 | 8.00 |
| Dihydroxyacetone | 2.50 | 3.00 | 5.00 | 3.50 | 3.50 | 0.50 | 0.50 | 5.00 |
| Isopropyl Palmitate | 2.25 | 2.25 | 2.25 | 2.25 | 2.25 | 2.25 | 2.25 | 2.25 |
| Stearic Acid | 2.00 | 2.00 | 2.00 | 2.00 | 2.00 | 2.00 | 2.00 | 2.00 |
| Thickening Agent | 1.50 | 1.50 | 1.50 | 1.50 | 1.50 | 1.50 | 1.50 | 1.50 |
| Glycol Stearate/Stearamide AMP | 1.20 | 1.20 | 1.20 | 1.20 | 1.20 | 1.20 | 1.20 | 1.20 |
| Dimethicone (DC 200) | 1.00 | 1.00 | 1.00 | 1.00 | 1.00 | 1.00 | 1.00 | 1.00 |
| Cationic Copolymer 7688 MP | 1.00 | 0.50 | 0.50 | 1.50 | 2.50 | 1.00 | 1.00 | 5.00 |
| PEG-100 Stearate | 1.00 | 0.50 | 0.50 | 1.00 | 1.00 | 0.75 | 1.00 | 1.00 |
| Glycerol Stearate | 0.55 | 0.50 | 0.50 | 0.80 | 0.55 | 0.55 | 0.30 | 0.30 |
| Cyclopentasiloxane/Dimethiconol (DC 1501) | 0.50 | 0.50 | 0.50 | 0.50 | 0.50 | 0.50 | 0.50 | 0.50 |
| Phenoxyethanol | 0.40 | 0.40 | 0.40 | 0.40 | 0.40 | 0.40 | 0.40 | 0.40 |
| Cetyl Alcohol | 0.30 | 0.30 | 0.30 | 0.30 | 0.30 | 0.30 | 0.30 | 0.30 |
| Methyl Paraben | 0.20 | 0.20 | 0.20 | 0.20 | 0.20 | 0.20 | 0.20 | 0.20 |
| Propyl Paraben | 0.10 | 0.10 | 0.10 | 0.10 | 0.10 | 0.10 | 0.10 | 0.10 |
| Water | balance | balance | balance | balance | balance | balance | balance | balance |

EXAMPLE 9

A set of experiments are here reported comparing the cationic copolymer of the present invention with related quaternary ammonium materials.

A base formula was utilized and different quaternary ammonium materials were added. The base is outlined in Table II below.

TABLE II

| Base Formula | |
|---|---|
| Component | Weight % |
| Glycerin | 12.0 |
| Dihydroxyacetone | 2.5 |
| Isopropyl Palmitate | 2.3 |
| Color Enhancing Agent | * |
| Stearic Acid | 2.0 |
| Glycol Stearate/Stearamide AMP | 1.2 |
| Silicones | 1.5 |
| PEG-100 Stearate | 1.0 |
| Glycerol Stearate | 0.5 |
| Phenoxyethanol | 0.4 |
| Fragrance | 0.4 |
| Cetyl Alcohol | 0.3 |
| Erythrulose | 0.3 |
| Methyl Paraben | 0.2 |
| Colorants | 0.2 |
| Propyl Paraben | 0.1 |
| Citric Acid | 0.1 |
| Tetrasodium EDTA (39% Active) | 0.1 |
| Gel Thickener | 0.1 |
| Deionized Water | Balance to 100 |

Four samples were prepared with different quaternary ammonium or control polymers in the base formula. Each of the samples was applied onto a forearm area of a subject at 20 mg/cm$^2$ dosage. The sample was allowed to dry on the skin for 3 minutes. Thereafter, the skin was rinsed under running water for 2 minutes.

Prior to treatment and eight hours subsequent thereto, the area of treatment was observed for coloration. Measurements were taken with a Hunter Lab Spectra Colorimeter, with values reported for L, a* and b*. Results are detailed in Table III.

TABLE III

| Sample | Color Enhancing Agent | L | a* | b* | Delta E | Observations |
|---|---|---|---|---|---|---|
| — | Initial Skin Value | 67.47 | 7.94 | 14.74 | — | |
| 1 | Simulgel NS (1.5%) (i) | 66.41 | 8.05 | 15.00 | 1.09 | Streaking |
| 2 | Distearyl Dimonium Chloride (0.2%) | 64.92 | 8.51 | 16.51 | 3.16 | Some streaking |
| 3 | Simulgel 7688 MP Cationic Polymer (1.5%) (ii) | 60.41 | 9.68 | 19.22 | 8.62 | No streaking |
| 4 | Distearyl Dimonium Chloride (0.2%) and Simulgel 7688 MP Cationic Polymer (1.5%) | 59.62 | 10.04 | 19.19 | 9.68 | No streaking |

(i) Simulgel NS is a Seppic trademark for hydroxyethylacrylate/sodium acrylodimethyltaurate polymer.
(ii) Simulgel 7688 MP is a Seppic trademark for acrylamide/acryloylethyl trimethylammonium chloride/tris(hydroxymethyl)acrylamidomethane copolymer.

Sample 1, which is a standard control, exhibited considerable loss of the tanning effect at the eight hour mark. There was also streaking of the tan. Sample 2 utilized a monomeric quaternary ammonium compound which is distearyl dimonium chloride. Color intensity loss (delta E) improved and less streaking was produced than the control. Sample 3 utilizing a crosslinked cationic copolymer per the present invention resulted in a significant enhancement of the tanning effect and no streaking was observed. An even further enhancement was seen in Sample 4. In this experiment the crosslinked cationic copolymer of the present invention was combined with a monomeric quaternary ammonium compound (distearyl dimonium chloride). Tanning effect retention was increased further and streaking was not observed. Based on these results, it is evident that the crosslinked cationic copolymer of the present invention operates as a color enhancing agent.

Further experiments were conducted to evaluate effects of different cationic polymers. These experiments were done several months subsequent to those under Table III and, therefore, exhibited slightly different initial skin values. In all other respects, the experiments were done in accordance with those for which the Table III results were obtained.

TABLE IV

| Sample | Color Enhancing Agent | L | a* | b* | Delta E | Observations |
|---|---|---|---|---|---|---|
| — | Initial Skin Value | 67.58 | 7.84 | 14.70 | — | |
| 5 | Simulgel NS (1.5%) (i) | 66.59 | 8.10 | 15.08 | 1.09 | Streaking |
| 6 | Aristoflex ® AVC(1.5%) (ii) | 66.53 | 8.03 | 15.14 | 1.15 | Streaking |
| 7 | Sepigel ® 305 (1.5%) (iii) | 66.61 | 8.15 | 15.02 | 1.06 | Streaking |
| 8 | Merquat ® 5 (1.5) (iv) | 65.07 | 8.42 | 16.44 | 3.08 | Some streaking |

(i) Simulgel NS is a Seppic trademark for hydroxyethylacrylate/sodium acrylodimethyltaurate polymer.
(ii) Aristoflex ® AVC is a Clariant Corp. trademark for Acryloyl Dimethyltaurate/Vinyl Pyrrolidone Copolymer.
(iii) Sepigel ® 305 is a Seppic trademark for Polyacrylamide.
(iv) Merquat ® 5 is a Nalco Corp. trademark for Acrylamide/Methacryloyloxyethyl Trimethyl Ammonium Methylsulfate Copolymer.

Table IV employs Sample 5 (equivalent to Sample 1) as a standard control. This material exhibited considerable loss of the tanning effect at the eight hour mark. There was also streaking of the tan. Sample 7 is a non-cationic polymer based on acrylamide monomer units. The relatively low delta E value indicates considerable loss of tan coloration upon rinse. Sample 8 is a cationic copolymer but differs from that utilized in Sample 3 by not having a crosslinking agent (i.e. tris (hydroxymethyl)acrylamidomethane). Sample 8 had a delta E of 3.08 which was much better than those of the nonionic polymers/copolymers in formulas represented by Samples 1, 5, 6 and 7. Moreover, there was also improvement in reducing streaking. Best performance was exhibited by Sample 3 which is a formula according to the present invention utilizing a cationic polymer. Sample 3 imparted to skin a significant enhancement of the tanning effect and no streaking was observed.

EXAMPLE 10

Experiments with but one exception identical to those of Example 9 were conducted and reported hereunder. The some base formula and Samples were utilized to evaluate differences in intensity of color prior to any rinse.

Table V and VI record two sets of color enhancement measurements (delta E), the latter set being performed several months subsequent to the former. In all other respects, the experiments of Tables V and VI were done identically.

TABLE V

| Sample | Color Enhancing Agent | L | a* | b* | Delta E |
|---|---|---|---|---|---|
| — | Initial Skin Value | 67.47 | 7.94 | 14.74 | — |
| 1 | Simulgel NS (1.5%) (i) | 65.39 | 8.31 | 15.62 | 2.29 |
| 2 | Distearyl Dimonium Chloride (0.2%) | 63.51 | 8.87 | 17.71 | 5.04 |
| 3 | Simulgel 7688 MP Cationic Polymer (1.5%) (ii) | 59.83 | 10.02 | 20.07 | 9.62 |

TABLE V-continued

| Sample | Color Enhancing Agent | L | a* | b* | Delta E |
|---|---|---|---|---|---|
| 4 | Distearyl Dimonium Chloride (0.2%) and Simulgel 7688 MP Cationic Polymer (1.5%) | 58.41 | 10.34 | 20.21 | 10.85 |

(i) Simulgel NS is a Seppic trademark for hydroxyethylacrylate/sodium acrylodimethyltaurate polymer.
(ii) Simulgel 7688 MP is a Seppic trademark for acrylamide/acryloylethyl trimethylammonium chloride/tris(hydroxymethyl)acrylamidomethane copolymer.

TABLE VI

| Sample | Color Enhancing Agent | L | a* | b* | Delta E |
|---|---|---|---|---|---|
| — | Initial Skin Value | 67.14 | 7.89 | 14.78 | — |
| 5 | Simulgel NS (1.5%) (i) | 65.41 | 8.35 | 15.64 | 1.99 |
| 6 | Aristoflex ® AVC (1.5%) (ii) | 65.18 | 8.33 | 15.60 | 2.10 |
| 7 | Sepigel ® 305 (1.5%) (iii) | 65.27 | 8.29 | 15.70 | 2.03 |
| 8 | Merquat ® 5 (1.5) (iv) | 62.98 | 8.88 | 17.75 | 5.19 |

(i) Simulgel NS is a Seppic trademark for hydroxyethylacrylate/sodium acrylodimethyltaurate polymer.
(ii) Aristoflex ® AVC is a Clariant Corp. trademark for Acryloyl Dimethyltaurate/Vinyl Pyrrolidone Copolymer.
(iii) Sepigel ® 305 is a Seppic trademark for Polyacrylamide.
(iv) Merquat ® 5 is a Nalco Corp. trademark for Acrylamide/Methacryloyloxyethyl Trimethyl Ammonium Methylsulfate Copolymer.

Sample 3 represents the present invention. Intensity of color change reached 9.62 (delta E). Addition of Distearyl Dimonium Chloride (0.2%) to the Simulgel 7688 Cationic Polymer (1.5%) resulted in a further coloration enhancement to 10.85 (delta E). See Sample 4. By comparison, Samples 5 and 6 representing nonionic acrylo type polymers managed only to increase the delta E to values of 1.99 and 2.10, respectively. Merquat® 5 which is a non-crosslinked cationic polyacrylamide and methacryloyl type polymer had an appreciable color intensity enhancement. Sample 8 exhibited a 5.19 delta E. However, the crosslinked cationic copolymer of Sample 3 exhibited a significantly higher delta E value.

What is claimed is:

1. A cosmetic product for imparting a glow or sunless tan to skin comprising:
   (i) from about 0.1 to about 20% by weight of a tanning agent which is reactive with skin to produce a tan color;
   (ii) from about 0.1 to about 20% by weight of a color enhancing agent which is a crosslinked cationic copolymer that is acrylamide/acryloylethyl trimethylammonium chloride/tris(hydroxymethyl)acrylamidomethane copolymer; and
   (iii) a cosmetically acceptable carrier.

2. The composition according to claim 1 wherein the tanning agent is dihydroxyacetone.

3. The product according to claim 1 wherein the crosslinked cationic copolymer is present in an amount from about 0.5 to about 10% by weight of the composition.

4. The product according to claim 1 wherein the tanning agent is present in an amount from about 0.5 to about 10% by weight of the composition.

5. The product according to claim 1 further comprising from about 0.01 to about 5% by weight of a monomeric quaternary ammonium salt.

6. The product according to claim 5 wherein the monomeric quaternary ammonium salt is a di($C_{12}$-$C_{22}$) fatty alkyl substituted ammonium salt.

7. The product according to claim 5 wherein the monomeric quaternary ammonium salt is distearyl dimonium chloride.

* * * * *